United States Patent [19]

Christie, Jr. et al.

[11] 4,093,991

[45] June 6, 1978

[54] SPECTROPHOTOMETER-DIGITAL DATA PROCESSING SYSTEM FOR APPEARANCE MEASUREMENTS PROVIDING FAST AND ACCURATE STANDARDIZATION, EASE OF USE FOR DIFFERENT APPEARANCE MEASUREMENTS AND FAST RESPONSE

[75] Inventors: John S. Christie, Jr., McLean; S. Upton Jenkins, Fairfax; George B. McConnell, Vienna, all of Va.

[73] Assignee: Hunter Associates Laboratory, Inc., Fairfax, Va.

[21] Appl. No.: 762,929

[22] Filed: Jan. 26, 1977

[51] Int. Cl.² .......................... G01N 21/22; G01J 3/02; G06F 15/20
[52] U.S. Cl. ................................... 364/525; 364/498; 356/96
[58] Field of Search ................ 235/151.3, 151.35, 150; 356/96–97, 173, 176, 177

[56] References Cited

U.S. PATENT DOCUMENTS

| | | | |
|---|---|---|---|
| 3,695,764 | 10/1972 | Delmas, et al. | 235/151.35 X |
| 3,701,601 | 10/1972 | Plumpe, Jr., et al. | 235/151.35 X |
| 3,878,378 | 4/1975 | Johnseo, et al. | 235/151.35 |
| 3,935,436 | 1/1976 | Holschlag | 235/151.35 |
| 3,986,776 | 10/1976 | George | 356/96 X |

Primary Examiner—Edward J. Wise
Attorney, Agent, or Firm—Charles W. Helzer

[57] ABSTRACT

A combined scanning spectrophotometer-digital data processing system including a microcomputer is described for making appearance measurements. The instrument is comprised by an optical sensing unit and a signal processing unit. The optical sensing unit utilizes a simulated D65 light source lamp together with an 8 inch diameter integrating light sphere for use primarily in the diffuse polychromatic illumination of reflectance test specimens but which also is used with transmittance test specimens. Light leaves the sphere through a transmittance port in which a transmittance test specimen may be disposed in the case of transmittance measurements. The light sphere further includes a reflectance port for making reflectance measurement of a test specimen placed at the reflectance port. Light from the reflectance test specimen leaves the sphere through the transmittance port along a single light beam path which is directed onto a rotating variable interference filter wedge for isolating the individual wave lengths over the visible spectrum. Light level at each wave length is sensed by a silicon diode electro-optic detector whose output is converted to digital signal form and together with a wave length identification signal supplied from a shaft encoder rotated synchronously with the rotating variable interference filter wedge monochromator, is supplied from the optical sensor unit to the signal processing unit. The signal processing unit utilizes a preprogrammed microcomputer and an operator controlled keyboard to quickly and easily perform zero adjust and standardization corrections together with other second order effect corrections and derives output measures of true reflectance, true transmittance, tristimulus color values, color scale values and color difference values. A printer or other display device is connected to the microcomputer to print out or display the spectrophotometric data or other tristimulus or color scale values representative of the appearance characterstics of either a transmittance or reflectance test specimen.

33 Claims, 9 Drawing Figures

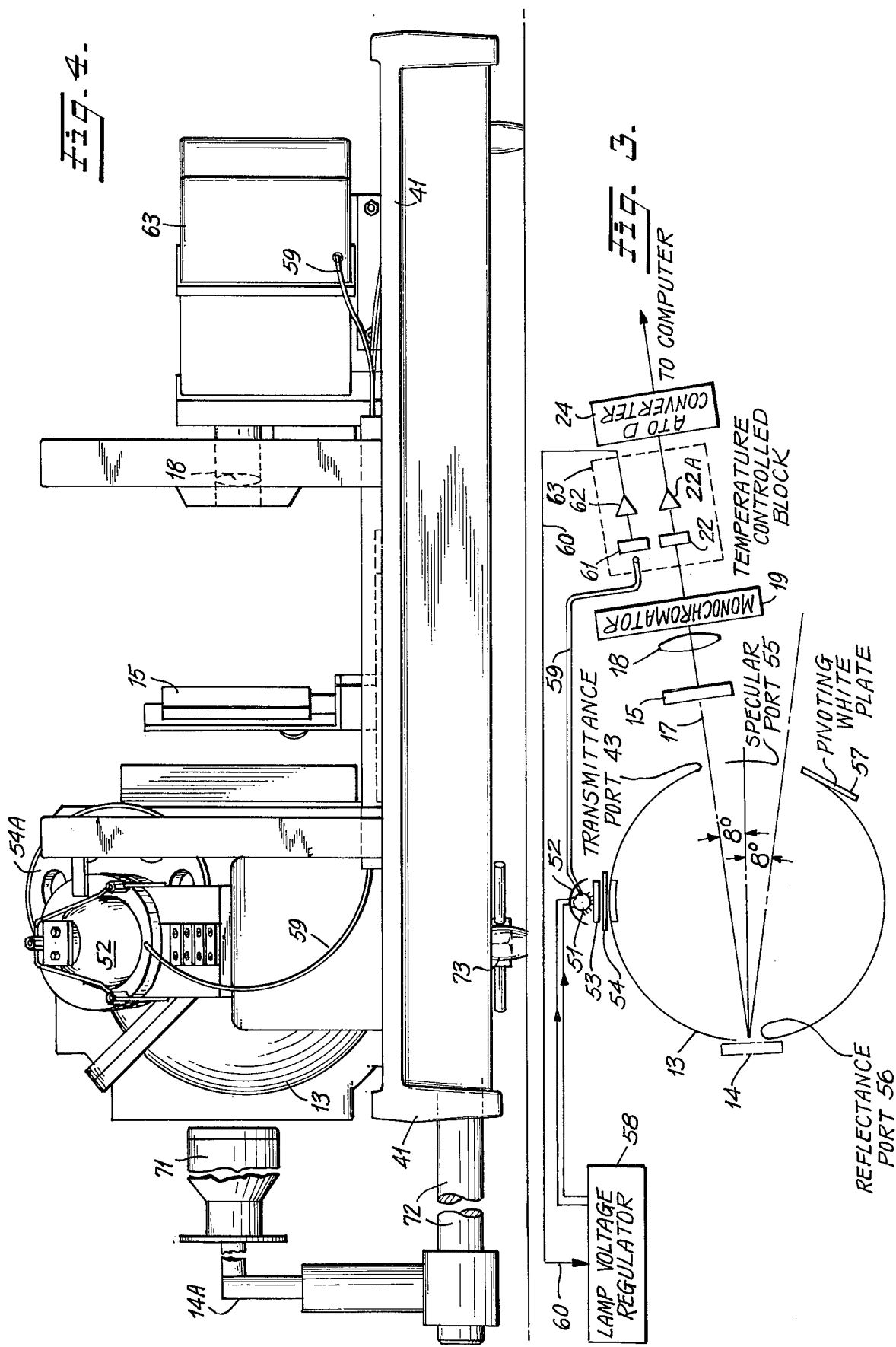

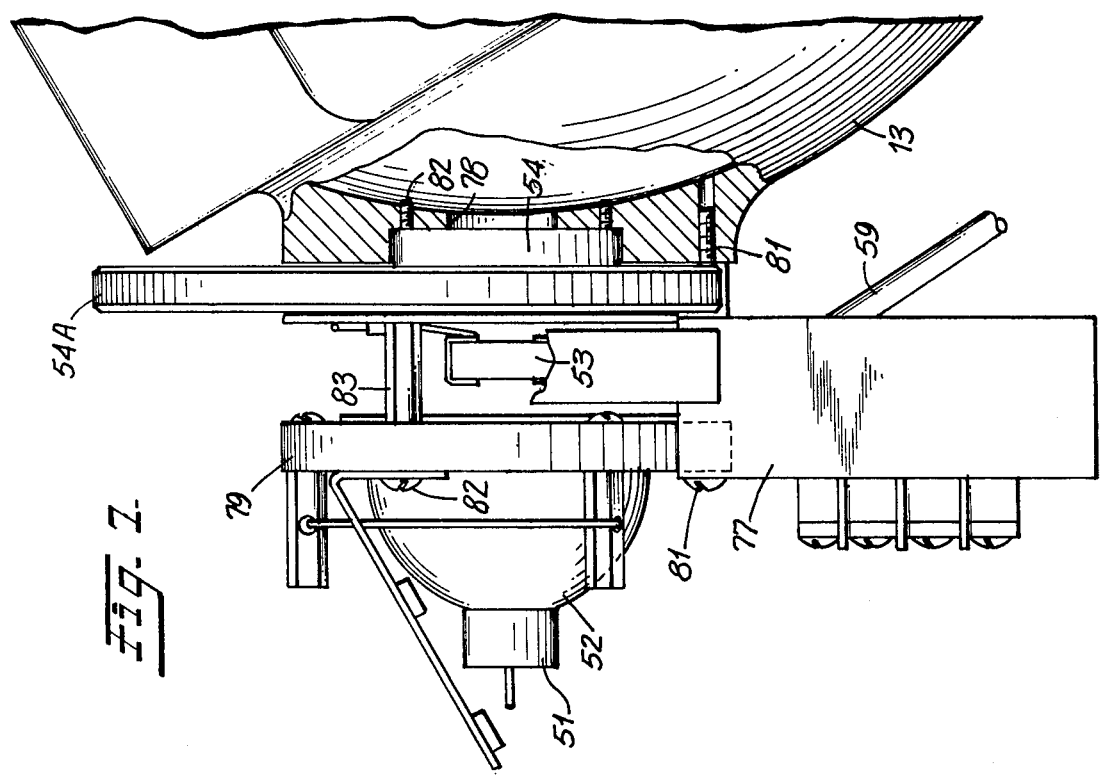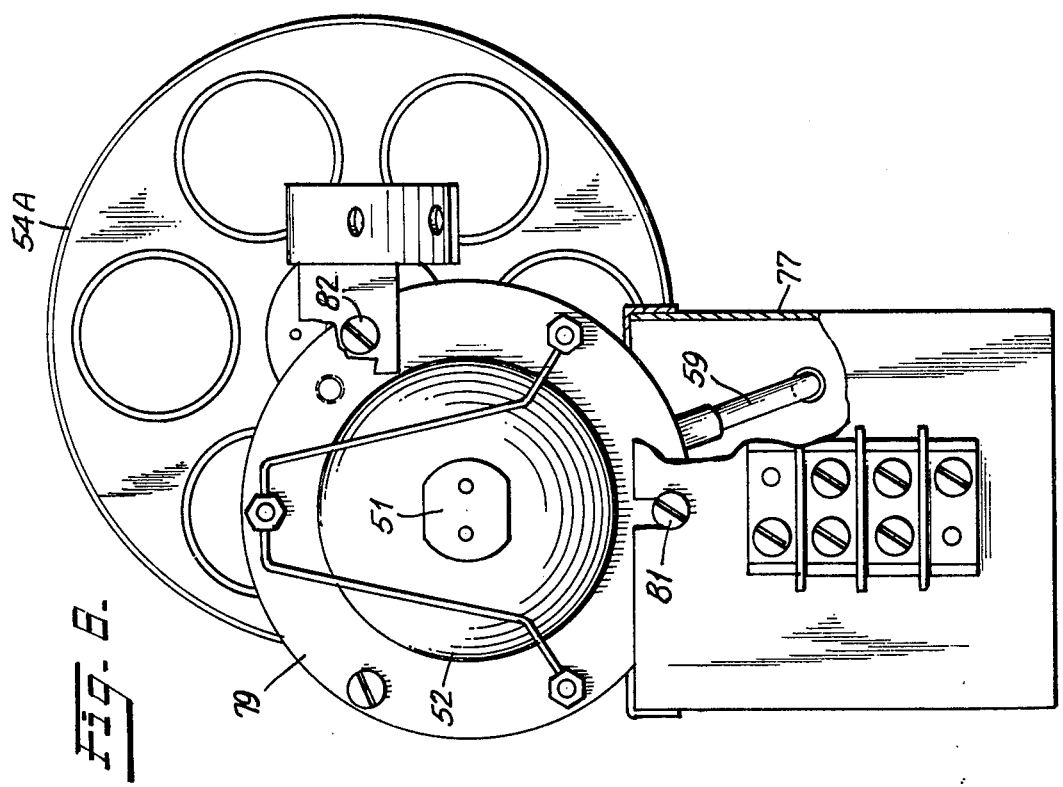

SPECTROPHOTOMETER-DIGITAL DATA PROCESSING SYSTEM FOR APPEARANCE MEASUREMENTS PROVIDING FAST AND ACCURATE STANDARDIZATION, EASE OF USE FOR DIFFERENT APPEARANCE MEASUREMENTS AND FAST RESPONSE

BACKGROUND OF THE INVENTION

1. Field of the Invention

This invention relates to a new and useful measuring instrument for simplifying the task of making appearance measurements of objects such as products of manufacture, foodstuffs and the like.

More specifically, the invention relates to a novel combined scanning spectrophotometer-microcomputer digital data processing system for processing, storing and performing fast computations with respect to digital data signals supplied from the scanning spectrophotometer sensor head to thereby quickly and easily calibrate (standardize) the instrument relative to predetermined appearance standards and for deriving a wide variety of output measurements in the form of visual displays, printed alpha numeric characters, graphs, or the like which are representative of the color and certain spatial properties of test specimen objects whose appearance is to be measured.

2. Prior Art Situation

In the textbook entitled "The Measurement of Appearance" by Richard S. Hunter, published by John Wiley & Sons, Publishers, New York, N.Y. - 1975, the manner and means by which measurements are made to determine human visual responses to the appearance of different objects, is described in detail. In this textbook a wide variety of different instruments is described for measuring either of the two main categories of appearance attributes, namely color, and the geometric attributes or properties of light emanating from an object being observed exemplified by reflection, transmission, haze, opacity, etc. To operate these instruments and obtain any degree of accuracy in the results requires skill. In addition, in order to derive meaningful information concerning the appearance of an object, a relatively large inventory of such different instruments would have to be maintained together with a suitable computation center capable of analyzing and processing the results of measurements obtained from the different instruments. In order to reduce the number of different types of measuring instruments that one has to maintain as well as the need for a separate computation facility in order to perform meaningful appearance measurements with respect to manufactured products or other objects, the present invention was devised.

SUMMARY OF THE INVENTION

It is therefore a primary purpose of the invention to provide a novel combined scanning spectrophotometer-microcomputer digital data processing system for processing, storing and performing fast computations with respect to digital data signals supplied by the scanning spectrophotometer to the microcomputer digital data processing system. The system can be quickly and easily calibrated (standardized) relative to predetermined appearance standards and can be operated by relatively unskilled personnel for deriving a selected group of output appearance measurements in the form of visual displays, printed alpha numeric characters, graphs or the like, which are representative of the color and certain spatial properties of a specimen object whose appearance is to be measured.

In practicing the invention a combined single beam scanning spectrophotometer-digital data processing system for appearance measurements is provided. The system includes stabilized means for illuminating a test specimen held within a specimen holder means for measurement of its appearance characteristics. The specimen holder means can be adapted to hold test specimens for measurement of either their transmittance or reflectance with or without specular components included. Output light modulated with the appearance characteristics information pertaining to a test specimen being examined, is derived and is projected along a single light beam path. A visible spectrum monochrometer means is disposed in the single light beam path for deriving a plurality of separate, different wavelength monochromatic light beams representative of the appearance characteristics of the specimen being examined. An electro-optic detector means is disposed in the path of the separate, different wavelength monochromatic light beams for converting the same to a plurality of different electric signals representative of the appearance characteristics of the test specimen. These electric signals are supplied to an analog-to-digital converter which converts the signals to digital form. A digital encoder means is operatively synchronized with the monochrometer means for deriving encoded digital electric output signals characteristic of the wave length of the respective different frequency monochromatic light beams. The two sets of digital electric signals thus derived are supplied to microcomputer digital data processing means for processing the digital electric output signals and deriving output display indications of the appearance characteristics of the specimen being examined.

The microcomputer digital data processing means includes standardizing value register means for storing standardizing values derived by placement of an appearance standard of the test specimens whose appearance is to be measured in the specimen holder means and deriving standardizing values from the standardizing specimen digital electric output signals obtained from the output of the analog-to-digital converter means while measuring the standard. The microcomputer digital data processing means further includes specimen register means for storing input test specimen signal values obtained from the output analog digital converter means and further includes central processing unit means for multipying test specimen signal values by the standarizing values stored in the standardizing value register means to thereby derive a standardized specimen signal output for display or other use which is representative of the appearance characteristics of a test specimen standardized relative to the appearance standard employed in deriving the standardizing values.

The microcomputer digital data processing means further includes zero adjust value register means for storing zero adjust values determined for transmittance measurements by placing an opaque member in the measurement light path in advance of the monochrometer and deriving zero adjust signal values for each of the plurality of separate different wavelength monochromatic light beam responses at the output of the analog to digital converter means. Alternatively, a light absorber or light trap is placed at the reflectance port for reflectance zero adjust value measurements. The zero adjust values are stored in the zero adjust register means for use by the central processing unit of the microcomputer which subtracts the zero adjust values from the raw input test specimen signal values prior to standardization.

The standardizing value register means comprising a part of the microcomputer digital data processing means preferably comprises a plurality of operator keyboard accessed standard assigned values register means for storing known standard values of transmittance, reflectance with specular reflectance components included and reflectance with specular reflectance components excluded for the appearance standard placed in the specimen holder means during derivation of the standardizing values explained above. The central processing unit of the microcomputer then serves to divide the standardizing specimen digital electric output signals obtained from the output of the digital to analog converter means with the appearance standard in place in the specimen holder means by the standard assigned values stored in the standard assigned value register means. The quotients thus derived then are used as calibration factor multipliers in the standardizing process and for this purpose are stored in a calibration factor multiplier register. Thereafter, during measurement of a test specimen, the calibration factor multipliers are the values used by the central processing unit of the microcomputer while standardizing specimen signal values obtained from the output of the analog to digital converter means while measuring a test specimen for its appearance characteristics.

The system is designed to measure at least the values of total transmittance, regular transmittance, reflectance with specular reflectance components included and reflectance with specular reflectance components excluded for each test specimen being processed. For this purpose the means for illuminating test specimens comprises an integrating light sphere having a light source that projects light through a suitable illuminant filter and illuminating port into the hollow white interior of the light sphere. The integrating sphere serves as a diffuse polychromatic light source for illuminating the test specimens. The integrating light sphere includes a light entrance port, a reflectance port, a transmittance port, and a specular port. The specular port is open to a light trap for measurements in which specular reflectance components are to be excluded from a reflectance measurement and is closed by a white plate cover when the specular component is to be included. To correct for the disparities in the diffuse light source caused by the various ports listed above, sphere efficiency computation equations are part of a permanent program stored in a read only memory and the equations are used while performing a reflectance measurement. The resulting sphere wall efficiency factors are multiplied by the reflectance reading after zero value adjustment and standardization as described above. In conducting regular transmittance measurements, the sphere characteristics are not influenced by the specimen, so that such efficiency factor corrections are not required in calculating true transmittance. When conducting total transmittance measurements, a correction factor may also be included to compensate for change in the transmittance port efficiency.

The system may be used with anyone of a number of known illuminants A, C, D65 or F (or other) which are independent of the means for illuminating the interior of the integrating light spehere during measurement of a test specimen. For this purpose, the system further includes read only memory (ROM) registers for storing C.I.E. $\bar{x}, \bar{y}, \bar{z}$ standard observer functions and the spectral power distribution functions for each illuminant used with the system. The respective registers are keyboard accessible to an operator of the system for supply of the functions to the central processing unit of the microcomputer along with the standardized and zero adjusted test specimen signal values. In the case of reflectance measurements, the test specimen signal values will be corrected for sphere efficiency as well. The central processing unit serves to multiply the C.I.E. functions times a selected illuminant, times the standardized and zero adjusted as well as sphere efficiency corrected test specimen signal values of reflectance or transmittance and sums the results obtained at 10 nanometer intervals over the visible spectrum to thereby derive the tristimulus C.I.E. - X, Y, Z, (1931) standard colorimetric system values of a test specimen for display or other use.

In addition to the above features, the system further includes operator keyboard accessed read only memory (ROM) uniform color scale program register means for permanently storing uniform color scale computation programs. These programs can be called up by an operator on the keyboard for deriving color scale values such as a variety of L, a, b: Y, x, y uniform color scale values automatically from the C.I.E. X, Y, Z tristimulus values. Hence, the central processing unit of the microcomputer automatically can derive desired color scale values from the prestored uniform color scale programs for each test specimen being measured in response to a selected uniform color scale program being called out by the operator of the system on the operator keyboard.

The scanning spectrophotometer-microcomputer digital data processing system further includes reference color scale register means for storing reference color scale values to be used in performing color difference measurements. The central processing unit of the microcomputer upon command operates to store color scale reference values in the reference color scale register means either by keyboard entry or alternatively by placement of a color reference in the specimen holder means with respect to which differences in color scale of the test specimens are to be measured. The central processing unit further serves to subtract the color scale reference values stored in the reference color scale register means from the test specimen color scale values derived pursuant to the operations described in the preceeding paragraphs to thereby derive color difference values between test and reference specimens for display or other use.

BRIEF DESCRIPTION OF DRAWINGS

These and other objects, features and many of the attendant advantages of this invention will be appreciated more readily as the same becomes better understood from a reading of the following detailed description, when considered in connection with the accompanying drawings, wherein like parts in each of the several figures are identified by the same reference character, and wherein:

FIG. 3 is a schematic functional diagram illustrating the construction of the single beam scanning spectrophotometer sensing head shown in FIG. 2;

FIG. 4 is a side view of the single beam scanning spectrophotometer sensing head;

FIG. 6 is a partial end view of a part of the scanning spectrophotometer sensing head and illustrates the construction of a light source and filter wheel for illuminating the interior of a hollow light integrating sphere comprising a part of the assembly;

FIG. 7 is a side view of the assembly shown in FIG. 6; and

DETAILED DESCRIPTION OF PREFERRED EMBODIMENT

Figure 1:
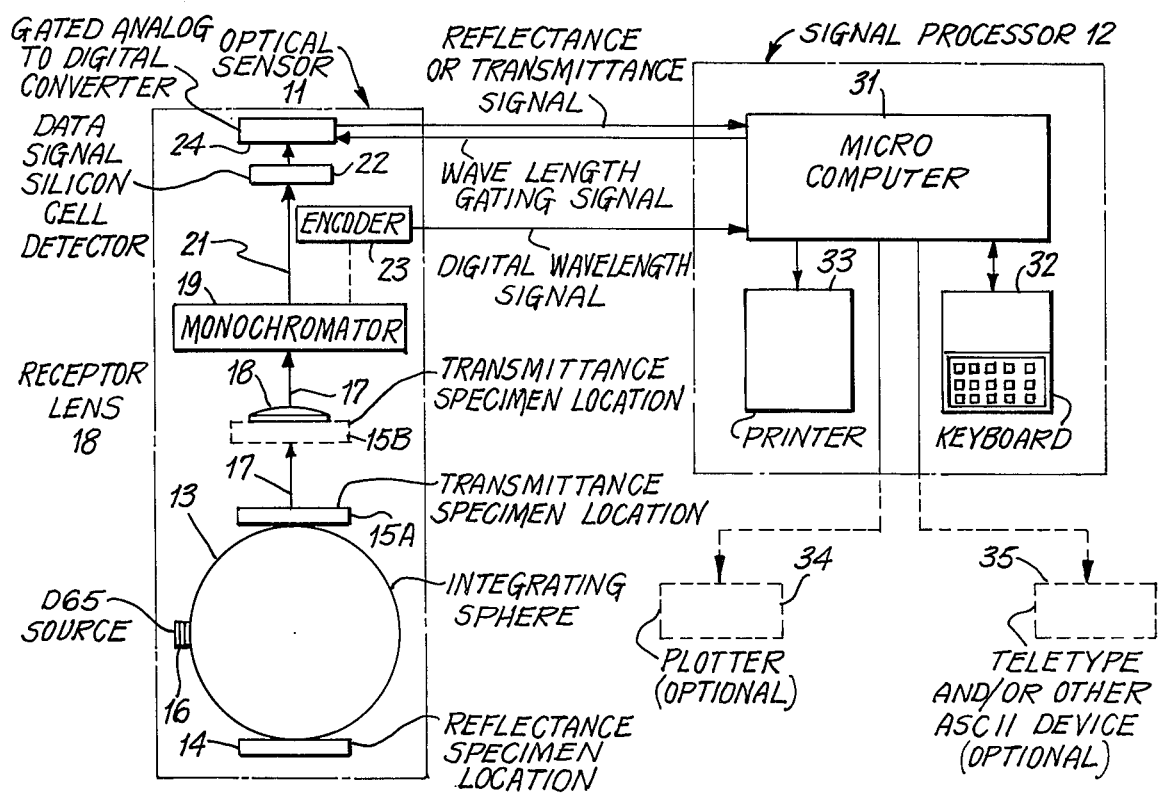
FIG. 1 is a schematic functional block diagram of a novel combined signal beam scanning spectrophotometer-microcomputer digital data processing system for appearance measurements constructed in accordance with the invention.

As shown in FIG. 1 of the drawings, the novel spectrophotometer-microcomputer digital data processing system according to the invention is comprised of two main parts, namely, an optical sensing unit hereinafter referred to as the optical sensor shown at 11 and a data signal processor unit shown at 12. The optical sensor 11 includes an illumination means comprised by an integrating light sphere 13 for illuminating either a reflectance specimen shown at 14 or a transmittance specimen which may be located either at 15a or 15b or at some intermediate point between these two extreme end positions. The integrating light sphere 13 is illuminated by a regulated, simulated daylight D65 source lamp 16 with attached reflector for projecting light into the interior of the integrating light sphere. The sphere provides diffuse polychromatic illumination for either the reflectance or transmittance specimens and produces output diffuse polychromatic light which leaves sphere 13 along a light transmission path 17. This light is picked up by a receptor lens assembly 18 including a field stop and projected in a finely focused beam onto a monochrometer means 19. Monochrometer means 19 isolates individual wavelengths of the polychromatic light projected thereon from the integrating light sphere 13 into a plurality of time separated (angular travel time of wedge), sequential, different wavelength monochromatic light beams. In the case of transmittance measurements, the light beam directed on the monochrometer 19 will have first passed through the transmittance specimen located at 15a or 15b or some intermediate position. While conducting measurements with reflectance specimens 14, the transmittance specimens 15 will be removed from the light path 17 so that the light reflected from the reflectance sample 14 modulates the light emanating from the integrating light sphere from the transmittance port which then is focused by the receptor lens assembly 18 onto monochrometer 19. In either type of measurement, the output single light beam directed by receptor lens assembly 18 onto monochrometer 19 will be modulated with the appearance characteristics information pertaining to a test specimen being examined.

The receptor lens assembly 18 includes a field stop and objective lens for producing a finely focused beam of light that is directed onto the monochrometer 19 whose construction and characteristics will be described more fully hereinafter. Briefly, however, it can be said that the monochrometer 19 comprises a rotatable, variable interference filter wedge of the type which is manufactured and sold by the Optical Coding Laboratories of Santa Rosa, California which is rotated at constant speed by a synchronous motor (not shown) in a manner such that the visible spectrum is scanned in approximately 1 to 3 seconds with the spectrum scan being repeated about every 2 to 7 seconds. Faster speeds of scanning are possible if a particular measurement situation requires it. The system response at any angular position of the rotatable variable wedge monochrometer is proportional to the reflectance (or transmittance) of the test specimen at the particular wavelength of light passed by the wedge at the angular position in question. For convenience, in the present invention the wavelengths at which readings are taken by the system are spaced evenly across the spectrum; however, because the spectrum scanning variable interference filter wedge is continuously variable, it is possible by special program options, to take readings at any desired wavelength within the visible spectrum from 380 to about 740 nanometers.

As it scans the spectrum, monochrometer 19 will derive a plurality of separate, different wavelengths monochromatic single light beams which are directed along the path 21 onto an electro-optical silicon cell detector 22. The separate, different wavelength monochromatic light beams will be sequentially separated in time by the period of time required to rotate the variable interference wedge monochrometer 19 thru an angular arc separating the different wavelength responsive portions of the wedge. The wavelength passed by each angular position on the wedge is identified by a shaft encoder 23 mounted on a common drive shaft with the monochrometer 19 so that it rotates synchronously with the monochrometer. The encoder 23 is designed to transmit at least 2,000 pulses per revolution of the monochrometer wedge 19. These pulses form digital wavelength identifying signal pulses that are supplied to the signal processor 12 to identify which angular position of the monochrometer wedge 19 is in position to supply a monochromatic light beam to the silicon cell detector 22. Detector 22 comprises an electrooptic detector means for converting the monochromatic light beams to a sequence of analog electric output signals representative of the appearance characteristics of a specimen being examined. These analog electric output signals are supplied to a gated analog to digital converter 24 which is of the successive approximation type with 14 bit binary resolution and 52 microsecond conversion time and is a commercially available integrated circuit device mounted on a circuit board together with timing and buffer circuits. The unit derives encoded digital electric output signals representative of the response of the silicon cell detector 22 at any given wavelength and transmits this data to the processor when so commanded by the processor. Because the shaft encoder 23 has identified to the signal processor 12 which angular position of the circular variable filter wedge (CVF) has rotated into the single light beam projected by receptor lens assembly 18, the signal processor can calculate the wavelength of light according to permanent data stored in a ROM register and which describes corrections to be made for non-linear characteristics of the CVF wedge. With this data the signal processor 12 is programmed to gate out the response of the analog-to-digital converter 24 only at desired wavelengths of light within the visible spectrum. Because of the fast responding nature of the instrument, multiple readings can be taken at each 10 nanometer interval in wavelength and 2 or more readings averaged by the signal processor 12. This provides an averaged reading of 2 or more successive readings about a centroid wavelength at 10 nanometer intervals throughout the visible spectrum. Thus, 32 averaged readings can be taken within the visible spectrum during each rotation of the variable wedge monochrometer 19. During normal appearance measurements, all 32 averaged readings will be gated out and supplied to the signal processor for each specimen being measured for its appearance characteristics. These signals are then processed to give true reflectance or transmittance values at each wavelength of light as will be described more fully hereinafter.

The signal processor 12 is comprised by a preprogrammed digital microcomputer 31 under the control of an operator keyboard 32 and providing its output to a printer 33 for printing out the spectrophotometric data and color scale values desired. Optional equipment may include a plotter 34 for plotting curves, graphs and the like representative of the appearance characteristics of a test specimen, and a teletype 35 or other ASC II device for remote operations.

Figure 2:
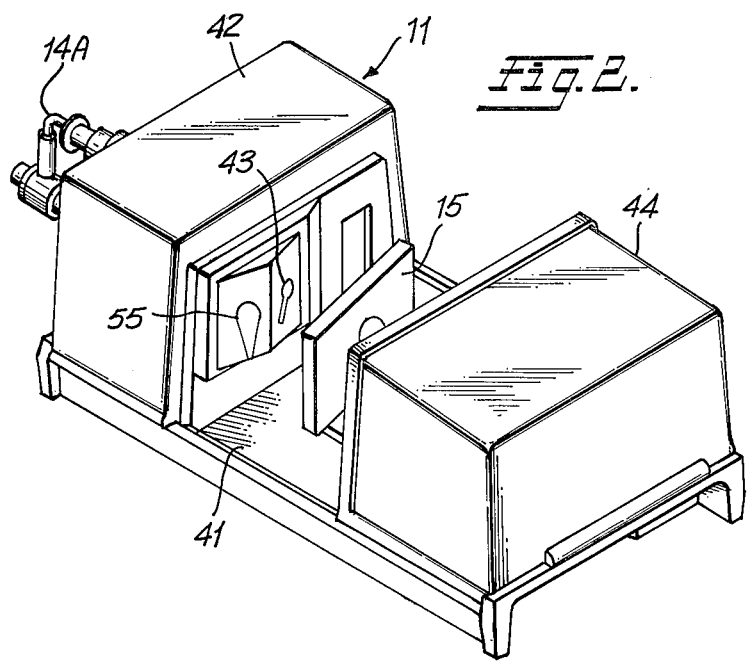
FIG. 2 is a perspective view of the single beam scanning spectrophotometer sensing head comprising one part of the system shown in FIG. 1.

From the above description considered in connection with FIG. 1, it will be appreciated that the optical sensor II contains three functional units; (a) the integrating light sphere 13 and its associated source lamp and filters, (b) the receptor lens assembly 18 together with the monochrometer 19 and shaft encoder 23, and (c) the silicon cell detector 22 and analog to digital converter 24. FIG. 2 of the drawings is a perspective overall view of the optical sensor assembly 11. The assembly is mounted on a suitable supporting base member 41 and comprises a first housing member 42 in which the integrating light sphere 13 and associated source lamp and filters is housed. Light emanating from the light sphere is projected through a transmittance port 43 along a path which passes through a transmission compartment defined by the space between the housing 42 and a second housing 44 containing the functional units (b) and (c). In transiting the transmission compartment, the light will pass through a transmittance test specimen if one is supported in the transmittance specimen holder 15. In the case of reflectance measurements, the reflectance test specimen is held against a reflectance port formed in the integrating light sphere on the back side of the housing 42 by a reflectance specimen holder 14A. Light from the sphere modulated by the reflectance specimen appearance characteristics leaves the sphere through the transmittance port 43. With no transmittance specimen in holder 15 an image of the reflectance sample will be directed onto the receptor lens assembly 18 and monochrometer 19 in housing 44. A cover (not shown) is provided for enclosing the transmission compartment when measurements are being run with the instrument.

The receptor lens assembly 18, rotatable monochrometer wedge 19, shaft encoder 23, silicon cell detector 22 and gated analog to digital converter 24 all are mounted within the second separate housing member 44 which also is supported on base member 41. The gated analog to digital converter output data signals, the wavelength identifying gating signals from microcomputer 31, and the wavelength identifying signals from encoder 23 to microcomputer 31, are supplied by interconnecting cables to the signal processing unit 12 which is housed in a separate cabinet from the optical sensor unit 11. The optical sensor 11 is designed in a manner such that it can be supported in an upright manner as shown in FIG. 2, or alternatively, can be mounted vertically with respect to the position shown or at some other angular relation relative to the horizontal position shown in FIG. 2. In order to accommodate the requirements of any particular transmittance measurement, the transmittance sample holder 15 is provided with a shelf, clamps, clips or the like for supporting specimens to be measured in the transmission path within the transmission compartment.

FIG. 3 is a schematic functional diagram illustrating the details of construction of the integrating light sphere 13 and showing its relation to the other elements of the optical sensor system. Sphere 13 is designed so that all specimens can be placed tangent to the sphere wall and are illuminated from an illuminating means including a suitable source of light. For most measurement, the source will be simulated D65 daylight produced by projecting light from a light source such as a quartz-halogen cycle tungsten lamp 51 projected by reflector 52 through an infra-red filter element 53 for eliminating infra-red specimen heating, through a D65 filter element 54, and thence through a suitable port or window into the interior of the integrating light sphere 13. Light sphere 13 has a white hollow interior which is highly reflecting and provides a highly diffuse polychromatic light for illuminating the test specimens.

In addition to the transmittance port 43, mentioned with respect to FIG. 2, sphere 13 further includes a specular port 55 and a reflectance port 56. A pivoting white plate shown at 57 is designed to be pivoted in position over the specular port 55 for closing this port while making measurements where it is desired to include specular reflectance components. The transmittance port is positioned 8° above the normal to the center line of the reflectance specimen and the specular port 55 is located 8° below this normal. Diffused light in the integrating light sphere 13 is modified either by a transmittance specimen 15 located in the light path 17 or by a reflectance specimen 14 located at the reflectance port 56. Modified reflected light from the surface of a reflectance specimen 14 exits the sphere 13 through the transmittance port 43 along the light path 17 on its way to the receptor lens 18 and monochrometer 19. The specular component of the surface reflected light from reflectance specimen 14 exits the sphere 13 through the specular port 55 provided the pivoting white plate 57 is rotated to leave the port open. Preferably a light trap is placed over the specular port 55 when measurements are being made in this manner to exclude the specular component of the reflected light. If the specular port 55 is covered by the pivoting white plate 57, the specular component will be included in a measurement being made.

When a transmittance test specimen 15 is placed in the path 17 for transmittance measurements, the other two ports are made to be part of the wall of the integrating light sphere 13 as closely as possible by placing a white tile at the reflectance port 56, and by covering the specular port 55 with the pivoting sheet 57. If the transmittance specimen 15 is placed flush against the transmission port 43, the total light transmitted through the specimen, diffuse as well as specular, will be included in the measurement being made. This is called total transmittance. If the transmittance specimen 15 is placed anywhere else in the transmission compartment along the optical path 17 between the transmission port 43 and the receptor lens assembly 18, less and less diffuse light will be included in the measurement. For maximum exclusion of the diffuse components, the transmittance specimen is placed as close as possible to the receptor lens 18 as depicted in 15B in FIG. 1. Such a measurement is called regular transmittance measurement.

In order to minimize to the greatest possible extent the effect of extraneous variables such as lamp voltage changes on the output measurements of the instrument, a lamp voltage regulator shown at 58 is provided for maintaining essentially constant luminosity despite supply line voltage variations, aging of the filament, etc. For this purpose, a feedback regulating loop is provided through a fiber optic light sensing coupling arrangement shown at 59. The fiber optic light sensor 59 has one end positioned to view the filament of the light source 51. The remaining end of the fiber optic light sensing element 59 is positioned to direct light onto the light sensitive surface of an electro-optic silicon detector cell 61. Cell 61 has its output supplied through an integrated circuit operational amplifier 62 back through a conductor 63 to regulate the operation of the lamp voltage regulator 58 in a manner so as to maintain the luminosity of the light produced by light source 51 substantially constant. Alternatively, the sensed lamp output can be directed from the fiber coupling 59 to the primary electro-optic detector 22 during periods when the spectrum is not being scanned. The microcomputer processor unit 12 would control the viewing sequence and would allow closed loop surveilance of the operation of the optical sensor unit 11 by the signal processor 12. Such an arrangement then would utilize only a single electrooptical detector for both signal sensing and maintenance of calibration, and hence would be more reliable and accurate.

As stated earlier, light from source 51 is projected through an infra-red absorbing (or reflection) filter element 53 and thence through a suitable illuminant filter element 54 such as the D65 illuminant filter. Filters for special purposes such as evaluating flourescent specimens are mounted in a filter wheel 54A to be described more fully hereinafter with relation to FIGS. 4–7 whereby their special filters can be changed by the operator to exclude certain portions of the spectrum. The D65 illuminant filter 54 and the infra-red heat absorbing filter 53 preferably are fan cooled to prevent heat buildup. A standby switch (not shown) is provided for reducing source voltage to the lamp 51 during standby when the instrument is not in use in order to prolong lamp life. In addition to the above features, the lamp voltage regulating silicon cell detector 61 and its associated amplifier 62 are mounted in a common temperature controlled block 63 along with the data signal sensing silicon cell detector 22 and its associated amplifier 22A whereby each of these elements can be temperature controlled to maintain optimum performance and minimize the effect of ambient temperature changes on the measured result obtained with the instrument.

Figure 5:
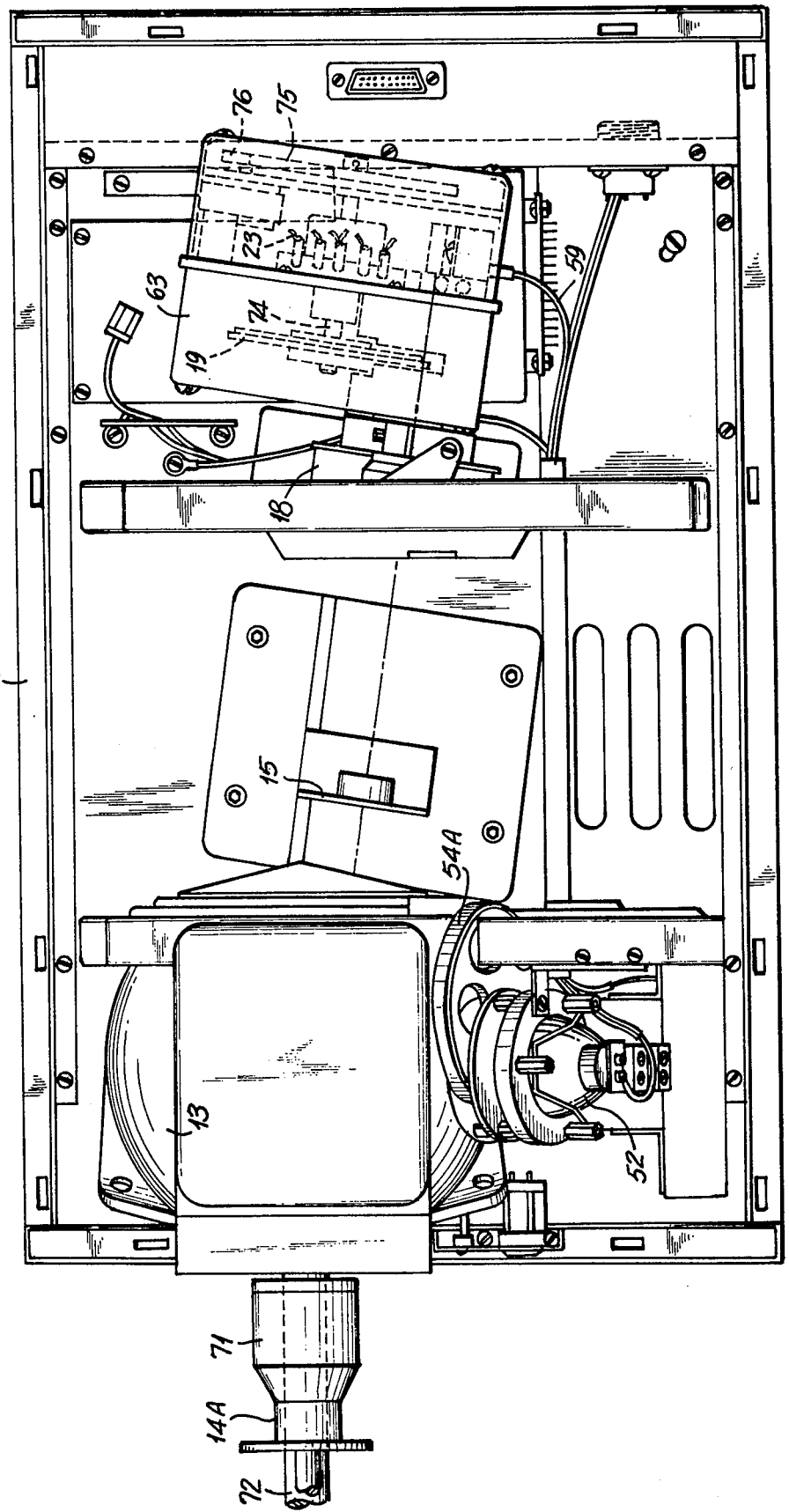
FIG. 5 is an upper plan view of the single beam scanning spectrophotometer sensing head showing certain essential features of the device in dotted outline form.

FIGS. 4 and 5 of the drawings are a side view and a top plan view, respectively, of the optical sensor assembly showing details of its construction. The integrating light sphere 13 is shown mounted on the left hand end of the supporting base member 41 with the light source and reflector 52 secured over the integrating light sphere 13 by suitable mounting brackets. A rotatable source filter mounting wheel 54A is interposed in between the light source and reflector unit 52 for rotating into position any desired one of a number of different source modifying filter elements mounted within the rotatable filter wheel 54A for use in floresecence measurements. The construction of the light source and rotatable filter wheel 54A will be described more fully hereinafter with relation to FIG. 6 and 7 of the drawings. The reflectance sample holder prefereably comprises a cup shaped member 71 having the configuration of an earphone and lined with a foam rubber or other similar material on the surface that opposes the reflectance port in integrating light sphere 13. The sample holding cup 71 is secured to the end of a post 14A, slidably supported on an extensible pipe 72 secured to the under carriage of base member 41 by a tightening screw-clamp 73. The cup shape sample holder 71 is designed to press a test specimen to be measured for its reflectance property against the reflectance port of integrating light sphere 13 where it will be illuminated by light diffusely directed thereon by the sphere. It is believed obvious that either flat specimens or solid specimens such as oranges, apples or the like all can be held by the specimen holding cup means 71 and pressed into position over the reflectance port for measurement.

The transmittance sample holder 15 is shown interposed in the light path 17 extending between the integrating light sphere 13 and the receptor lens assembly 18. When reflectance measurements are being conducted, removal of the transmittance test specimens from the holder 15 will provide a clear optical path to assure uninterrupted optical coupling between the transmittance port of the integrating light sphere and the receptor lens assembly 18. The continuously variable, rotatable interference filter monochrometer wedge 19 is shown mounted on a common drive shaft 74 with the shaft encoder 23. The entire assembly is driven by a friction driven wheel 75 that in turn is driven by a smaller peripherally arranged idler drive wheel 76 that is driven in turn by a constant speed synchronous motor (not shown). Light directed through the monochrometer interference wedge 19 impinges upon the silicon cell detector 22 which is mounted adjacent to the light source regulating silicon cell detector 61 in a common housing member 63 that is thermally regulated to maintain temperature of these two elements within prescribed ranges set by the manufacturers of the devices. The fiber optical coupling 59 for viewing the light source filament is best seen in FIG. 4 of the drawings.

FIGS. 6 and 7 of the drawings illustrate the manner in which the light source 51 and reflector 52 together with the infra-red filter 53, D65 daylight filter 54 and rotatable source modifying filter holder 54A are mounted with respect to the integrating light sphere 13. The light source 51 and reflector 52 are secured as a unit by a supporting member 77 which is mounted adjacent a window opening 78 in a flatened planar outer segment of the wall of the integrating light sphere 13. A D65 daylight source filter 54 is secured over window 78. The lamp 51 and reflector 52 are supported in an annular flange member 79 secured to the top of support member 77 by a machine bolt 81. The machine bolt 81 also extends into the planar segment of the exterior surface of the integrating light sphere for providing rigidity to the structure and also for spacing apart the structure a predetermined distance from the outer segment surface of the integrating light sphere 13 in which the window 78 is formed. A second threaded machine bolt 82 also serves the same purpose and in addition supports a sleeve 83 on which the rotatable circular filter element holder 54A is journaled. The infra-red filter element 53 is held in place in the space intermediate the light source reflector assembly 51, 52 and the rotatable source modifying filter support wheel 54A by means of finger clamps which in turn are secured in place by the machine bolt 82 and sleeve 83. The space enclosing this assemblage is provided with cooling air by a suitable ventilating fan (not shown) for drawing in air from outside the outer housing member 42 shown in FIG. 2 and flowing it past the light source 51, reflector assembly 52, infra-red filter element 53, the source modifying filter support wheel 54A and the D65 daylight source filter 54. In addition to the standard D65 daylight source filter 54, the source modifying filter wheel element 54A is designed to have mounted in it additional source modifying filter elements that a user of the instrument might desire to mount in the support wheel for ready use.

The monochrometer 19 is a circular variable interference filter wedge having approximately a 2% bandpass (2% of a centroid wavelength) and covers the useful visible spectrum from about 380 nanometers to about 740 nanometers. A test specimen area of approximately 1 inch in diameter is imaged on the aperture formed in the stop in front of the circular variable wedge monochrometer by a 50 mm focal length, $f/1.6$ projection lens. The circular variable wedge and shaft encoder are driven by a common drive shaft from a synchronous motor through a friction drive wheel arrangement geared so that the visible spectrum is scanned in about 3 seconds. The shaft encoder generates 500 pulses per revolution which is resolved to 2000 parts per revolution by a quadrature circuit. This provides approximately 880 pulses over the useable range of the circular variable wedge of from 400 to 710 nanometers or around 3 pulses per nanometer and results in a wavelength resolution of about $\frac{1}{3}$ nanometers. The circular variable wedge is calibrated using arc source spectral lines or other suitable means as a reference and data relating bandpass centroid versus angular position of the circular variable wedge is computed for each desired wavelength. For convenience, centroid wavelengths spaced apart by 10 to 20 nanometers have been chosen for detection and processing although the instrument readily could be programmed to sense and process output data signals for any desired wavelength. Initially, the variable circular wedge is mechanically aligned in the instrument by locating one wavelength position on the variable circular wedge with an arc source spectral line or laser beam of a known monochromatic wavelength. Shaft encoder pulses required to locate other spectrum points then readily can be calculated using this point as a reference. The wavelength versus angular position of the circular variable wedge thus calibrated is stored in a wavelength calibration data register shown in FIG. 8A of the drawings.

Figure 8A:
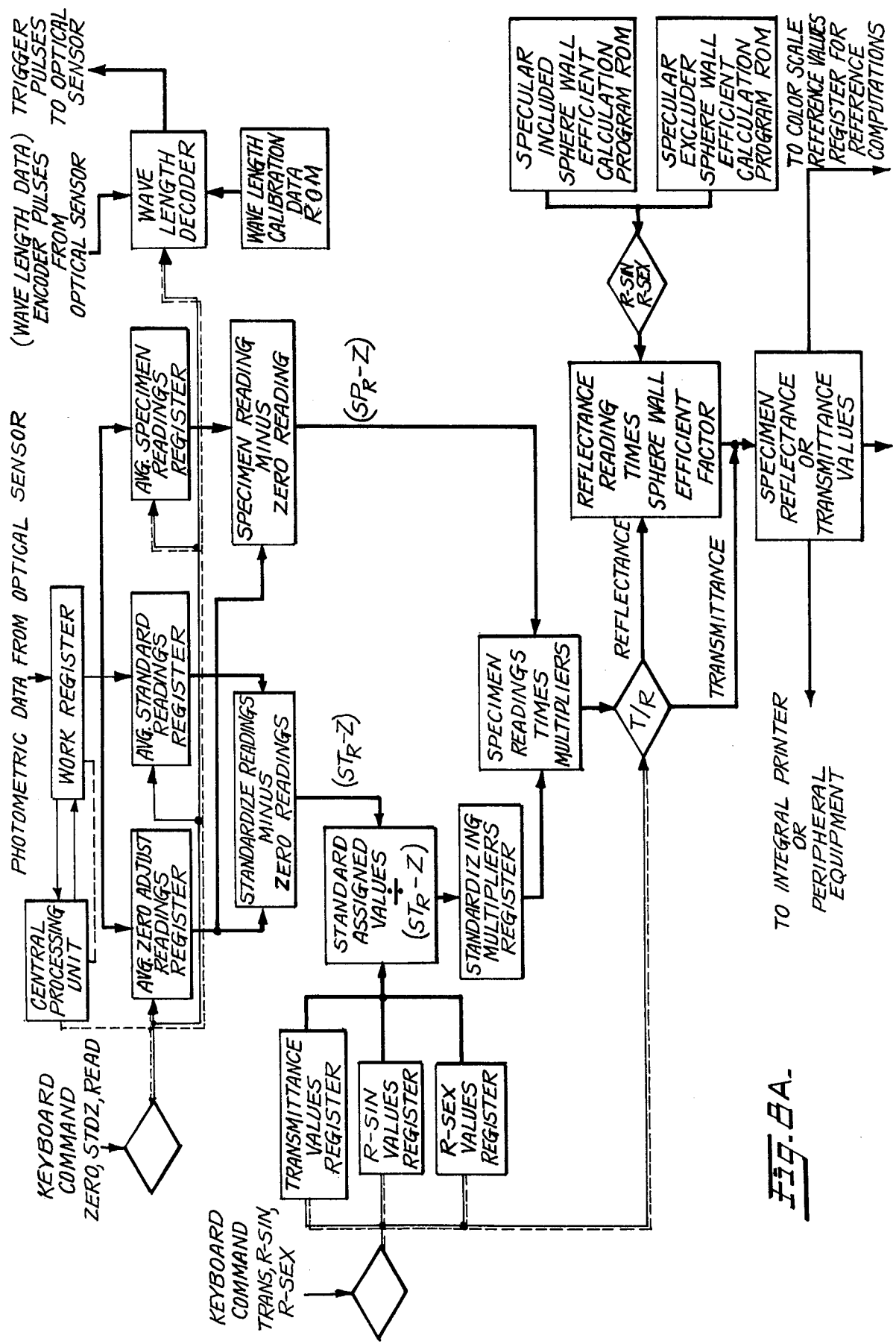
FIG. 8A and 8B comprise hybrid flow chart and partial functional block diagrams illustrating special features of construction of a microcomputer digital data processing system comprising a part of the invention.
Figure 8B:
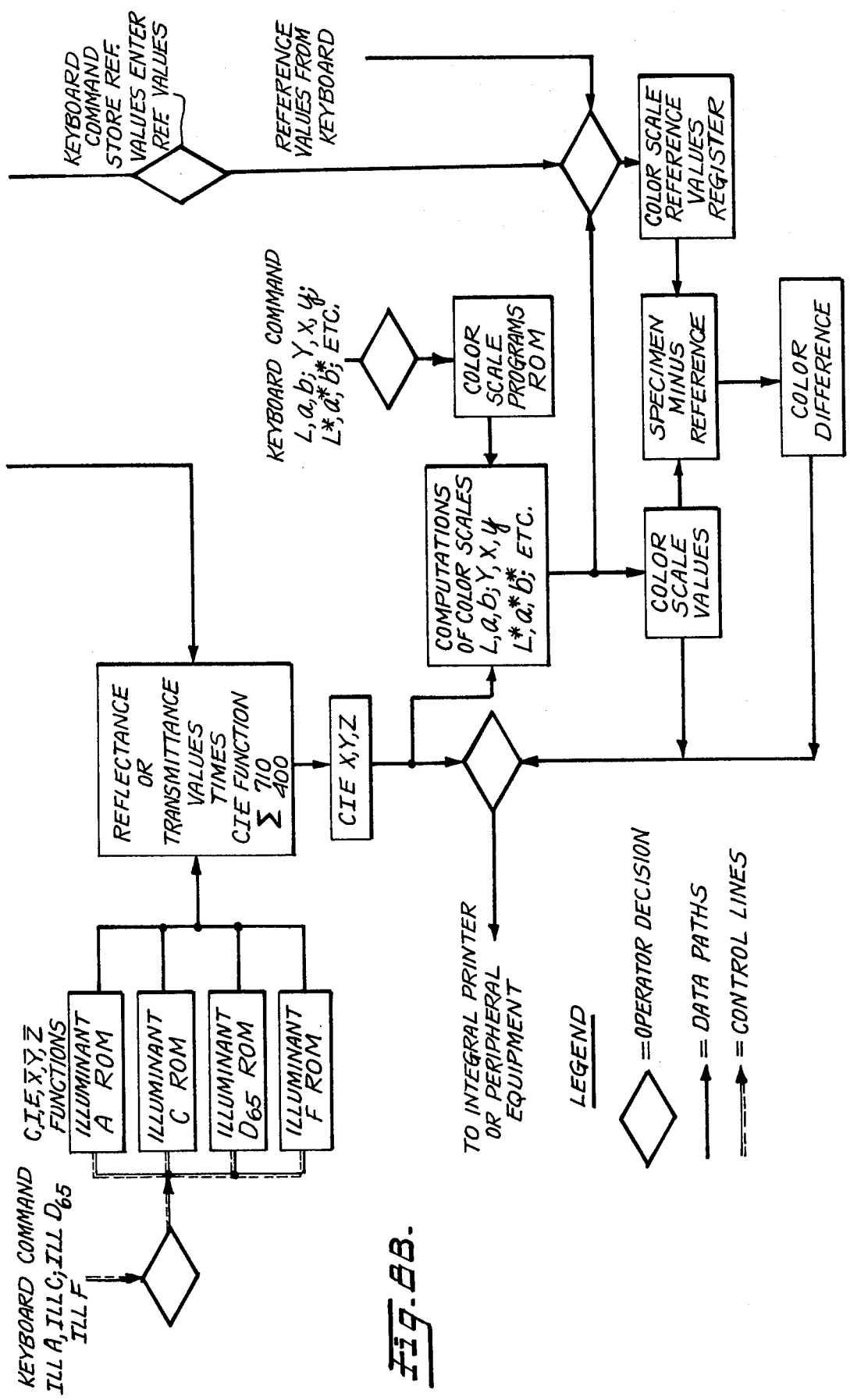

FIG. 8A is a hybrid functional block diagram-flow chart of a special purpose computer formed by appropriately programming a conventional, commercially available microcomputer such as the SBC 80-10 microprocessor manufactured and sold by the Intel Corporation. This microprocessor has built into it certain memory which can be programmed in the sense that the contents cannot be keyboard changed by an operator of the unit although the contents of such memory can be changed, but only by special effort, not through the keyboard. Such memory is referred herein to as "read-only-memory" (ROM) registers and the wavelength calibration memory constitutes just a ROM register. The wavelength calibration data upon command will supply its contents to a wavelength decoder circuit which also receives from the shaft encoder 23 of the optical sensor digital signal pulses indicative of the angular position of the rotatable circular variable wedge monochrometer 19. The wavelength decoder corrects for non-linear characteristics of the circular variable filter wedge monochrometer and compares the two sets of data to derive output gating trigger pulses for supply to the gated analog to digital converter 24 in the optical sensor. Hence, photometric data characteristic of a selected wavelength of light will be supplied from the gated analog to digital converter into the working register of the microcomputer digital data processing system at a selected angular position of the monochrometer. At this point in the description, it will be well to note that the wavelength decoder in a hardware sense may very well be a part of the central processing unit of the microcomputer system. However, for convenience and illustration, The operation performed by the wavelength decoder has been illustrated separately as shown in FIG. 8A in order that the flow of the data processing taking place in the microcomputer will be apparent. In this sense, FIG. 8A and 8B constitute hybrid functional block diagrams-flow charts since certain of the blocks shown in FIG. 8A and 8B are functions performed in the central processing unit in conjunction with the working register and other blocks are special purpose registers for either the permanent or temporary storing of data signals or other values and are specially designed into the signal processor.

The variable circular interference filter wedge 19 is rotated at a speed which covers the useful portion of the visible spectrum from 400 to 710 nanometers wavelength in about 3 seconds. This converts to a speed of scanning of about 100 nanometers per second. The analog to digital converter may, for example, comprise an MP 2814-4A3C A to D converter manufactured and sold by the Analogic Corporation which can convert the received data in about 75 microseconds. This makes possible 40,000–60,000 readings in one 3 second scan of the spectrum so that a large number of data points can be taken centered on a given centroid wavelength. Individual readings can be taken with only about 0.06 nanometer change in wavelength centroid during the four readings centered on each given centroid wavelength and the readings averaged for that centroid wavelength. This will then provide 32 averaged centroid wavelength readings for each revolution of the rotatable circular variable interference filter wedge monochrometer. By using such averaged readings, considerably greater precision can be obtained with the instrument than heretofore has been obtainable. The averaging of the individual readings around each centroid wavelength is performed by the central processing unit working in conjunction with the working register and the averaged readings then stored in one of the registers depending upon the type of reading in question, namely whether it is a zero value reading, a standard reading or a specimen reading as explained hereinafter.

As an alternative to the preferred method of deriving specimen, standard or zero readings which are the average of 3 or 4 wavelength readings centered around a centroid wavelength, it is also possible to derive, store and use in obtaining an output appearance measurement with the instrument, signals averaged over several revolutions of the circular variable interference filter wedge monochrometer. The scanning period of the visible spectrum can easily be reduced to less than 1 second if so desired. A complete revolution of the circular variable wedge monochrometer then would require the order of 2 seconds.

For certain types of appearance measurements, it may be desireable to obtain the average of several readings of a centroid wavelength averaged over several revolutions of the circular variable wedge monochrometer. The obtaining of such averaged readings is of course merely a matter of appropriate programming and instructions to the central processing unit. For the most part, however, it is desireable to employ the average wavelength measurement obtained as described above with respect to a given centroid wavelength within a single revolution of the circular variable wedge monochrometer.

The ability to obtain the average of several readings about each centroid wavelength of which there are 32 centroid wavelengths scanned in one revolution of the circular variable interference filter wedge, is an important and novel operating characteristic made possible by the design of the optical sensor unit. It will be noted that the optical sensor employs a single, fast responding, silicon semiconductor light detector cell together with a fast responding analog to digital converter for converting appearance characteristics information modulated on the centroid wavelength monochromatic light beams into digital electric signals. No light chopper or switching circuits or rectifier and filter networks are required which would slow down the response time of the instrument. Consequently, much faster response times are achieved with the present single beam monochrometer system than heretofore have been obtainable. This feature also reduces the complexity of the data signal processing by the data processor unit and facilitates the use of high speed microcomputer digitial data processing of the data obtained from the output of the optical sensor unit. An additional important advantage of the single beam design is that since the standard and the specimen occupy (by substitution) precisely the same position in the optical system, both are exposed to exactly the same illuminating and viewing conditions. This is not true in dual beam systems. Finally, there are substantially no alignment or calibration problems encountered in the use of the optical sensor unit since all zero adjusting, standardizing (calibration) is done automatically by the data processing unit as will be appreciated more fully hereinafter.

The construction and operation of the microcomputer comprising the heart of the digital data signal processing unit 12 is shown more fully in FIGS. 8A and 8B. The microcomputer-data porcessor receives raw reflectance or transmittance data signals from the optical sensor unit which are identified in FIG. 8A by the label entitled "photometric data from optical sensor". This data is temporarily stored in a working register and processed by the central processing unit to derive the desired averaged readings as explained above. By appropriate alignment of the optical sensor unit through the placement of an opaque member either in the transmittance path between the integrating light sphere 13 and the receptor lens aperture plate assembly 18 or a light trap over the reflectance port, zero adjust values can be obtained from the photometric data supplied from the optic sensor with the opaque member in place. These readings are then averaged by the c.p.u. and the average zero adjust reading values are stored in the average zero adjust readings register.

Included with the instrument as part of its equipment are two reflectance standards (one grey and one white) and four transmission filters for use in calibration (standardization) of the instrument. Known reflectance standard values for the white reflectance standard, both with specular component included (R-SIN) and with the specular component excluded (R-SEX) similary are permanently stored in the R-SIN standard assigned values register and the R-SEX standard assigned values register, respectively. These values are supplied from the factory and are derived from direct comparison with master standards traceable to measurement at the National Bureau of Standards. They are identified as standard assigned values and are employed in standardizing (calibrating) the instrument at the commencement of each appearance measurement run. In addition, calibration record cards are provided from the factory showing the instrument reading values for both the white and gray reflectance standards and for four transmission filters and are entitled "Values Read at Factory". These readings indicate the calibration of the instrument at the time it left the factory and can be used in checking calibration to detect any changes in the response of the instrument, particularly with regard to wavelength scale accuracy.

Before making a measurement run with the instrument, a standard white tile is used in connection with reflectance measurements to calibrate the instrument. With the white standard in place at the reflectance port, in response to a standardizing command from the operator with the keyboard, the processor obtains 32 averaged readings across the visible spectrum from the standard tile and subtracts the 32 values of the zero adjust readings in the zero adjust register. The zero adjusted standard reading values then automatically are divided by either R-SIN or R-SEX standard assigned values for reflectance standard measurements with specular component included or excluded, as the case may be. These values are known values for the standard and are prestored in the R-SIN and R-SEX assigned values registers. The resultant quotients are then stored in a standardizing multipliers register for use as calibration factor multipliers in standardizing all further test specimen readings conducted with the instrument.

When deriving the zero adjust readings value as described above, it is important that a light trap be placed over the reflectance port 56 of integrating light sphere 13 and that the pivoting white plate 57 be closed over the specular port 55. Also the transmission compartment defined by the space between the two housing members 42 and 44 shown in FIG. 2 should be closed with its cover. Thereafter, all further measurements whether standard values measurments or test specimen measurements should be conducted with this cover in place over the transmission test compartment.

In obtaining the standard readings values for transmittance measurements, the instrument is aligned as described in the preceeding sentences and with the opaque mask in place in the transmittance specimen holder the zero adjust readings are derived and stored in the zero adjust register. The opaque mask then is removed from the transmittance specimen holder. The standardize key is then pressed on the keyboard and the instrument will be standardized relative to air as a 100% transmittance standard and the standardizing multipliers stored in the standardizing multipliers for use as calibration factor multipliers while making subsequent test specimen transmittance measurements. In the case of transmittance measurements no standard assigned values are used for ratioing to determine the calibration factor multipliers. The 100% transmittance readings themselves are stored and used as the calibration factor multipliers. With respect to the standard readings obtained with the instrument with one of the standard filters in place in the transmittance specimen holder means, the standard filter filter readings are used only as calibration measurements.

As an alternative to the use of the preprogrammed standard assigned values as described above, it is possible to enter standard assigned values of transmission or either type of reflectance by keyboard entry. With this routine the standard assigned values of the standard to be used are keyed in for each centroid wavelength every 10 nanometers from 400 to 710 nanometers. When all standard assigned values have been entered, the standardizing key on the keyboard is pressed and the instrument will be standardized on the standard assigned valves entered through the keyboard. Subsequent specimen measurements then automatically will be directly related to this calibration.

As an example of the above, the procedure for obtaining standardizing reflectance measurements with specular component excluded (R-SEX) requires the placement of a light trap at the reflectance port and the pivoting white plate is removed from over the specular port 55 of the integrating light sphere 13. With the light trap at the reflectance port, the zero background energy values are then derived for each centroid wavelength across the spectrum by pressing the zero adjust key of the instrument. The light trap is then removed from the reflectance port and a white calibrated standard is inserted in its place at the reflectance port centered and in the up position. The assigned reflectance values of this white calibrated tile will have been stored in the processor ROM R-SEX assigned values register as described previously. The standardized button in then depressed and the instrument automatically will be standardized on the stored values of the white standard and subsequent specimen measurements automatically will be directly related to this calibration. In the event that it is desired to enter the standard assigned values for a particular standard not previously permanently stored in the memory of the microcomputer processor, then such values will be keyed in for each of the 32 centroid wavelengths as described previously in advance of the above procedures.

For measurements with the specular component included, the pivoting white plate is rotated in the position over the specular port. If the specular component is to be excluded, the pivoting white plate will be rotated to its open position, and specular component allowed to exit the port into a light trap. The test specimen then is placed in position over the reflectance port. To enter a specimen identification number on the printout, the "PRINT" key on the keyboard is depressed together with a suitable alphanumeric identification for the test specimen. The "READ" button is then depressed.

In deriving reflectance measurements output signals, the reflectance signals after multiplication by the standardizing calibration factor multipliers stored in the standardizing multipliers register, is further processed through multiplication by a sphere efficiency factor. These factors are derived from two separate equations sub-routines which are identified as specular included sphere efficiency factor and specular excluded sphere efficiency factor. The central processing unit of the microcomputer, upon direction to perform either type of reflectance measurement, automatically will multiply the standardized and zero adjusted reflectance reading by the appropriate computed sphere efficiency factor for each wavelength and thereafter supply the corrected results as the true reflectance values with either the specular component included or specular component excluded. These values are then supplied to a printer or other peripheral equipment for recordation if the system is so directed by the operator. The values also are supplied to further calculation stages for color scale computations, color difference computations and the like as well as will be described hereinafter with respect to FIG. 8B.

When measuring the transmittance of test specimens, the instrument is standardized for transmittance measurements as described above. With the pivoting white plate over the specular port and a white tile or plate placed over the reflection port of the integrating light sphere. If the transmittance measurements are to be made with diffuse illumination (total transmittance), the transmission test specimen holder is placed so that the specimen is flush against the transmittance port. If unidirectional illumination is desired (regular transmittance), the test specimen holder is placed so that the specimen is as close to the receptor objective lens as possible. The test specimen identification number is printed by keying in a suitable identification which may be alphabetic as well as numeric as selected on the printout selection keys of the keyboard. The test specimen is then placed in the transmission test specimen holder at the desired location and the "READ" key is depressed. The true value of transmittance will then be printed out on the printer or supplied to other peripheral equipment as directed by the keyboard operator.

In conducting the above reflectance measurements, the true reflectance specimen reading (TRUE $R_{SPCM}$) is given by the following equation (1) for reflectance:

$$\text{TRUE } R_{SPCM} = \left( \frac{TR_{STD}}{ST_R - Z_R} \right)(SP_R - Z_R) \text{ (SPHERE EFF. FACTOR)} \quad (1)$$

The standard equation for the true transmittance specimen reading TRUE $T_{SPCM}$ is given by the following equation (2) for transmittance:

$$\text{TRUE } T_{SPCM} = \left( \frac{\text{TRUE } T_{STD}}{ST_T - Z_T} \right)(SP_T - Z_T) \quad (2)$$

In equation (1) $TR_{STD}$ is the assigned value of reflectance for the standard, $ST_R$ is the voltage reading obtained from the standard, $Z_R$ is the zero adjust voltage and $SP_R$ is the voltage reading obtained from the specimen. In equation (2) TRUE $T_{STD}$ is the assigned value of transmittance for the standard, $ST_T$ is the transmittance voltage reading obtained from the standard and $Z_T$ is the zero adjust voltage value.

From the above standard equations, it will be appreciated that the expression (TRUE Reading$_{Standard}$/-

Standard reading - zero reading) provides the quotients obtained by dividing the standard assigned value by the zero adjust standard reading and comprise the calibration factor multipliers stored in the standardizing multipliers register. In the case of the transmittance reading, the sphere efficiency factors do not enter into the reading and hence do not appear in the expression for the true transmittance measurements.

From the foregoing description, it will be appreciated that the microcomputer-data processor receives raw reflectance or transmittance test specimen signal values from the optical sensor unit. The processor then corrects this raw data for zero value offset, for spectral response of the entire optical system measured relative to a known standard, and when reflectance is being measured, it corrects for sphere efficiency, and derives a resultant output signal for display or other use which is a measure of absolute reflectance or transmittance. To perform the above operations, the keyboard command which controls the operation of the instrument is divided into essentially three different sections: (a) measurement mode selection in which the parameters of the measurement to be made are set by entry through the keyboard; (b) printout selection in which, after the measurement has been made, the type of printout desired, or scale to be computed, as chosen through keyboard entry; and (c) option selection in which access to various optional features with which the instrument may be equiped, is provided.

In addition to the above-described basic functions, the microcomputer digital data processor, on command from the keyboard, can perform the following optional functions. It can perform tristimulus calculations by the 10 nanometer weighted ordinate method for any or all of four different illuminants. It can also compute color values for any selected color spaces and values of small color difference. With added options, computations can be performed for various indicies of whiteness, yellowness, or even a general index of metamerisms. FIG. 8B of the drawings illustrates certain of these optional functions which are subject to the control of the keyboard operator.

The microcomputer, digital data processor is programmed to perform 10 nanometer weighted ordinate method tristimulus integration of transmittance or reflectance values to arrive at tristimulus X, Y, Z values. These X, Y, Z values simulate the color matching response functions of the human observer as defined by the 1931 CIE 2° Standard Observer discussed in detail in the above noted "The Measurement of Appearance" textbook by Richard S. Hunter. Tristimulus integrations based on any or all four standard illuminants (A, C, D65, F) may be keyboard selected by the operator. The color values computed by the microcomputer processor are relative to the absolute value of the perfect white diffuser as measured under the same geometric conditions (ASTM method 306), according to the recommendation of the International Commission on Illumination of Jan. 1, 1969.

As shown in FIG. 8B Tables of the CIE (Commission Internationale de L'Eclairage, the main international organization concerned with problems of color and color measurement) functions $\bar{x}$-. $\bar{y}$-$\bar{z}$- as defined in the above "Measurement of Appearance" textbook are stored in respective ROM registers. Tables of spectral power distribution values for illuminants A, C, D65 and F also are stored in respective ROM registers. In response to input keyboard commands by the operator, the appropriate illuminant tables of values is selected for processing by the central processing unit using the tables of CIE $\bar{x}$, $\bar{y}$, $\bar{z}$ functions in performing the weighted ordinate method of tristimulus integration over the visible spectrum from 400 nanometer wavelength to 710 nanometer wavelength. These calcualtions are performed with respect to the measured true values of reflectance or transmission of a test specimen and the resultant CIE X Y Z tristimulus values derived for supply to the printer, display or other use. These values also can be retained in the working register of the microcomputer for use in computation of color scales as described hereafter in addition to being printed out or otherwise displayed.

The CIE X Y Z tristimulus values can be employed in conjunction with a desired one of a number of different color scale programs which are pre-stored in a ROM color scale programs register. Any selected one of the pre-stored color scale programs is accessible by keyboard command to control operation of the CPU in the computation of color scale values in accordance with the Hunter L, a, b method, the CIE 1976 L*a*b* method, the modified Adams-Nickerson (ANLAB) method; the FMC-2 (FRIELE-MacAdam-Chickering) color difference calculation method; or other techniques as described in the above referenced "The Measurement of Appearance" textbook by Richard S. Hunter. The Hunter L, a, b, program, for example, gives measurements of color in units of approximate visual uniformity throughout the color solid. L measures the lightness and varies from 100 for perfect white to zero for black approximately as the eye would evaluate it. The chromaticity dimensions (a) and (b) give understandable designation of colors in the following manner. (a) measures redness when plus, grey when zero and greeness when minus. (b) measures yellowness when plus, grey when zero and blueness when minus. Upon command from the keyboard operator, a desired one of the color scale programs is called out of the color scale programs register and controls operation of the central processing unit to derive the desired color scale values which then are displayed, printed out or otherwise used.

If it is desired to obtain comparisons between the color scale values derived in the above-described manner with respect to some reference sample, this can be achieved with the microprocessor by two different techniques. One technique is to enter known color scale reference values into a color scale reference value register from the keyboard through appropriate entry by an operator. Upon command, the specimen color scale value will then have the reference values subtracted from them and the differences displayed, printed out or otherwise used as representative of a color difference between a test specimen and the reference values. A second technique available is to take a reading of the reference specimen with the optical sensor to derive its standardized and zero adjusted values in the manner described above. The reflectance data from the reference specimen then is stored in a reference register for later calculation of the color difference information from values derived from subsequently measured test specimens. The color scale difference values will then be supplied to the printer, or other display, or can be used directly in a process control application to control color batch formulation, or the like. In a similar manner, through appropriate entrys from the keyboard differences in the CIE tristimulus X Y Z values (ΔX, ΔY, ΔZ); L, a b values ΔL, Δa Δb; or the like, can be obtained through appropriate command to the microcomputer-processor.

In addition to the above-described functions, the microcomputer-digital data processor can be programmed to perform any desired series of instructions since it is actually a general purpose digital microcomputer having aditionally built-on memory capacity in the form of random access memories for storing selections of several keyboard commands in such a way that one key can be depressed to perform a series of other keyboard commands. Writing of such programs is flexible depending upon the results desired. For example, any selected order or readout of preprogrammed rountines for measurements can be called up in any desired order for presentation and use. If desired, a diagnostic program for leading an operator through a number of diagnostic checks on the instrument for maintaining calibration of the instrument, readily can be programmed into the microcomputer. The enhanced flexibility allowed by the combined sensor head-microcomputer digital data processor facilitates use of the instrument in many different appearance measuring applications both for measurement purposes as well as process control applications where widely different formats in the nature of the specimens to be monitored and in the output may be required. The instrument possesses great versatility in accommodating second order and other effects such as the sphere substitution error correction provided for reflectance measurements, etc. By appariate programming of the microcomputer digital data processor, many different special applications and corrections for higher order effects can be accommodated.

From the foregoing description, it will be appreciated that the invention provides a novel combined scanning spectrophotometer-microcomputer digital data processing system for measuring, processing, storing and performing fast computations with respect to digital data output signals supplied from a scanning spectrophotometer optical sensor head. The arrangement is such that the instrument can be quickly and easily calibrated (standardized) relative to predetermined appearance standards and is capable of deriving a wide variety of output measurements for visual display, printing of alpha-numeric records, plotted graphs and the like or for use in automatic control systems, all in a unitary compact instrument that does not require an external data processing facility.

Having described a preferred embodiment of a novel combined scanning spectrophotometer-microcomputer digital data processing system for appearance measurements according to the invention, it is believed obvious that other modifications and variations will be suggested to those skilled in the art in the light of the above teachings. It is therefore to be understood that changes may be made in the particular embodiment of the invention disclosed which are within the full intended scope of the invention as defined by the appended claims.

What is claimed is:

1. A combined single beam scanning spectrophotometer-digital data processing system for appearance measurements including in combination stabilized illumination means, specimen holder means, means for illuminating a specimen to be examined supported by said specimen holder means for its appearance characteristics with said stabilized illumination means and for producing an output single beam of light modulated with appearance characteristics information pertaining to the specimen being examined, visible spectrum scanning monochromator means disposed in said appearance information modulated single beam of light for deriving a plurality of separate different wavelength monochromatic single light beams representative of the appearance characteristics of a specimen being examined, electro-optic detector means disposed in the path of said separate different wave length monochromatic light beams for converting the same to a plurality of separate different electric signals representative of the appearance characteristics of a specimen being examined, analog to digital converter means electrically coupled to said electro-optic detector means for converting the electric signals to digital form, digital encoder means operatively synchronized with said monochromator means for deriving encoded digital electric output signals characteristic of the wave length of each different frequency monochromatic light beam, and digital data processing means responsive to said analog to digital converter means and said digital encoder means for processing said digital electric outputs and deriving output electric signals for display or other use indicative of the appearance characteristics of a specimen being examined.

2. A scanning spectrophotometer-digital data processing system for appearance measurements according to claim 1 wherein said digital data processing means includes at least standardizing value register means for storing standardizing values derived by placement of an appearance standard of the specimens whose appearance is to be measured in the specimen holder means and deriving standardizing values from the standard specimen output signals obtained from the output of the analog to digital converter means while measuring the standard, specimen register means for storing input specimen signal values obtained from the output of the analog to digital encoder means and representative of the appearance values of a test specimen being measured, and central processing unit means for multiplying the specimen signal values by the standizing values to thereby derive a standardized specimen signal output for display or other use which is representative of the appearance characteristics of a test specimen standardized relative to the standard.

3. A scanning spectrophotometer-digital data processing systme for appearance measurements according to claim 2 wherein said digital data processing means further includes zero adjust value register means for storing zero adjust values determined by placing an opaque member in the light measurement path in advance of the monochromator means, means for deriving zero adjust signal values for each of the plurality of separate different wave length monochromatic light beam paths from the output of the analog to digital converter means with the opaque member still in place, and means for storing the zero adjust values in the zero adjust register means, said central processing unit means serving to subtract said zero adjust values from said input specimen signal values prior to standardization.

4. A scanning spectrophotometer-digital data processing system for appearance measurement according to claim 2 wherein the standardizing value register means comprises a plurality of operator keyboard accessed standard assigned values register means for storing predetermined standard values of transmittance, reflectance with specular reflectance components included and reflectance with specular reflectance components excluded for the appearance standard place in the specimen holder means during derivation of the standardizing values, said central processing unit means serving to divide the standardizing specimen digital electric output signals obtained from the output of the digital to analog converter means with the appearance standard placed in the specimen holder means by the predetermined standard assigned values stored in the standard assigned value register means and deriving the quotient, calibration factor multiplier register means comprising a part of the standardizing register means for storing the quotients for use as calibration factor multipliers in the standardizing process, said calibration factor multipliers being the values used by the central processing unit means while standardizing specimen signal values obtained from the output of the analog to digital converter means while measuring a test specimen for its appearance characteristics.

5. A scanning spectrophotometer-digital data processing system for appearance measurements according to claim 4 wherein said digital data processing means further includes zero adjust value register means for storing zero adjust values determined by placing an opaque member in the light measurement path in advance of the monochromator means, means for deriving zero adjust signal values for each of the plurality of separate different wavelength monochromatic light beam paths from the output of the analog to digital converter means with the opaque member still in place, and means for storing the zero adjust values in the zero adjust register means, said central processing unit means serving to subtract said zero adjust values from said input specimen signal values prior to standardization.

6. A scanning spectrophotometer-digital data processing system for appearance measurements according to claim 5 wherein said system is designed to measure at least the characteristics of transmittance, reflectance with specular components included and reflectance with specular components excluded for each test specimen being processed and further including illuminating light efficiency factor calculation program register means for both reflectance measurements, said central processing unit means further serving to process reflectance measurement signals derived according to claim 5 by a respective reflectance specular included or reflectance specular excluded illuminating light efficiency factor calculation program derived from said light efficiency factor register means to thereby derive a true reflectance measurement corrected for the effect of the specimen on illuminating light intensity.

7. A scanning spectrophotometer-digital data processing system for appearance measurements according to claim 5 wherein said system further includes C.I.E. $\bar{x}$, $\bar{y}$, $\bar{z}$ function read only memory register means for storing the C.I.E. $\bar{x}$, $\bar{y}$, $\bar{z}$ functions for each illuminant used with the system, respective illuminant tables of spectral power distribution value register means, said register means being keyboard accessible to an operator of the system for supply to the central processing unit means along with the standardized and zero adjusted test specimen signal values representative of the appearance characteristics of a test specimen being measured, said central processing unit further serving to multiply the respective C.I.E. function, times the selected illuminant spectral distribution values, times the standardized and zero adjusted test specimen signal values of reflectance or transmittance as the case may be and summing the results obtained over the visible spectrum to thereby derive the tristimulus C.I.E. X, Y, Z, Standard Colorimetric System values of a test specimen for display or other use.

8. A scanning spectrophotometer-digital data processing system for appearance measurements according to claim 7 wherein said system is designed to measure at least the characteristics of transmittance, reflectance with specular reflectance components included and reflectance with specular components excluded for each test specimen being processed and further including illuminating light efficiency factor calculation program register means for both reflectance measurements, said central processing unit means further serving to process reflectance measurement signals derived according to claim 7 by a respective reflectance specular included or reflectance specular excluded illuminating light efficiency factor calculation program derived from said light source efficiency factor register means to thereby derive a true reflectance measurement corrected for the effect of the specimen on illuminating light intensity.

9. A scanning spectrophotometer-digital data processing system for appearance measurements according to claim 8 further including operator keyboard accessed preprogrammed uniform color scale program register means for permanently storing uniform color scale computation programs for deriving color scale values L, $a$, $b$; Y, $x$, $y$ and the automatically from the C.I.E. X, Y, Z tristimulus values derived by the central processing unit means according to claim 8, said central processing unit means further serving to derive the color scale values L, $a$, $b$; Y, $x$, $y$, and the like of a test specimen for display or other use automatically in response to a selected uniform color scale program called out by an operator of the system from the uniform color scale program register means.

10. A scanning spectrophotometer-digital data processing system for appearance measurements according to claim 9 further including reference color scale register means for performing color difference measurements, said central processing unit means upon command serving to store color scale reference values in said reference color scale register means obtained from a color reference placed in the specimen holder means with respect to which differences of test specimens in color scale are to be measured, operator controlled keyboard operated means for alternatively storing keyboard entered color scale reference values in said reference color scale register means, and said central processing unit means further serving to subtract the color scale reference values stored in the reference color scale register means from the test specimen color scale values derived pursuant to claim 9 to derive color difference values between the test and reference specimens for display or other use.

11. A scanning spectrophotometer-digital data processing system for appearance measurements according to claim 1 wherein said stabilized illuminating means comprises a hollow integrating light sphere having a white interior into which light from a suitable light source is projected through an illuminating light beam port formed in the integrating light sphere, said integrating light sphere further having a light transmittance port formed therein and comprising a diffuse light source from which diffuse light emanates through the transmittance port along a transmittance path onto the receptor lens assembly for projection onto the monochrometer means and also including a reflectance measurement port formed on the opposite side of the integrating light sphere from said transmittance port, said specimen holder means further including transmittance test specimen holding means for supporting a transmittance test specimen in the diffuse single light beam path intermediate the transmission port in the integrating light sphere and the monochrometer means and removable during reflectance measurements, and further including reflectance test specimen holding means for holding a reflectance test specimen against the reflectance port of said integrating light sphere during reflectance measurements.

12. A scanning spectrophotometer-digital data processing system for appearance measurements according to claim 11 wherein said integrating light sphere further includes a specular reflectance component port formed in the wall of the integrating light sphere opposite the reflectance port and an equal angular distance of the order of 8 degrees displaced from a normal center line to the reflectance port starting at the intersection of the normal center line with plane of the reflectance port and with the transmittance port being displaced an equal number of degrees from the normal center line to the reflectance port in the same plane that contains a normal center line to the specular port whereby reflected light from the surface of a reflectance test specimen positioned at the reflectance port of the integrating light sphere exits the sphere through the transmittance port along the transmission path to the monochrometer means and the specular component of the reflected light from a reflectance test specimen exits the integrating light sphere through the specular port provided the specular port is open for making reflectance measurements with the specular reflectance component excluded, and highly reflecting while plate means for closing the specular port during reflectance measurements with the specular reflectance component included.

13. A scanning spectrophotometer-digital data processing system for appearance measurements according to claim 12 wherein said stabilized illumination means comprises fiber optic light sensing means for viewing the light emitting filament of the light source, light source stabilization system electro-optic detecting means responsive to light directed thereon from said fiber optic light sensing means viewing the light source filament and illuminating the light source voltage regulating means responsive to the output from said light source stabilizing system electro-optic detecting means for stabilizing operation of the illuminating light source and maintaining its luminosity within a prescribed range of values.

14. A scanning spectrophotometer-digital data processing system for appearance measurements according to claim 1 wherein said visible spectrum scanning monochrometer means comprises a circular variable continuous interference filter wedge covering the visible spectrum from 400 to 710 nanometers wavelength, said digital encoder means comprises a shaft encoder, means for continuously rotating said circular continuous interference filter wedge at a constant speed synchronously with the shaft encoder on a common drive shaft whereby the separate different frequency monochromatic light beams are sequentially separated in time, and further including means for gating out the encoded digital electric output signals characteristic of the wavelength of each different frequency monochromatic light beam from the analog to digital converter means at selectable wavelength intervals.

15. A scanning spectrophotometer-digital data processing system for appearance meaasurements according to claim 14 wherein said stabilized illumination means comprises a hollow integrating light sphere having a white interior into which light from a light source is projected through a suitable light source filter element disposed over an illuminating light beam port formed in the wall of the integrating light sphere, said integrating light sphere further having a light transmittance port formed therein and comprising a diffuse light source from which diffuse polychromatic light emanates through the transmittance port along a transmission path onto the receptor lens assembly for projection onto the monochrometer means and also including a reflectance measurement port formed therein on the opposite side from said transmission port, said specimen holder means further including transmittance test specimen holding means for supporting a transmittance test specimen in the diffuse light transmission path intermediate the transmittance port of the integrating light sphere and the monochrometer means, said transmittance test specimen being removed during reflectance measurements, and reflectance test specimen holding means for holding a reflectance test specimen against the reflectance port of said integrating light sphere during reflectance measurements.

16. A scanning spectrophotometer-digital data processing system for appearance measurements according to claim 15 wherein said integrating light sphere further includes a specular reflectance component port formed in the wall of the integrating light sphere opposite the reflectance port and displaced an equal angular distance of the order of 8 degrees from a normal center line to the reflectance port starting at the intersection of the normal center line with the plane of the reflectance port and with the transmittance port being displaced an equal number of degrees from the normal center line to the reflectance port in the opposite direction in the same plane that contains a normal center line to the specular port whereby reflected light from the surface of reflectance test specimen positioned at the reflectance port of the integrating light sphere exits the sphere through the transmittance port along the transmission path to the monochrometer means and the specular conponent of the reflected light from a reflectance test spcimen exits the integrating light sphere through the specular port provided the specular port is open for making reflectance measurements with the specular reflectance component excluded, and highly reflecting white plate means for closing the specular port during reflectance measurements with the specular reflectance component included.

17. A scanning spectrophotometer-digital data processing system for appearance measurements according to claim 16 wherein said stabilized illumination means comprises fiber optic light sensing means for viewing a light emitting filament of an illuminating light source, light source stabilization system electro-optic detecting means responsive to light directed thereon from said fiber optic light sensing means viewing the light source filament and illuminating light source voltage regulating means responsive to the output from said light source stabilizing system electro-optic detecting means for stabilizing operation of the illuminating light source and maintaining its luminosity within a prescribed range of values.

18. A scanning spectrophotometer-digital data processing system for appearance measurements according to claim 17, wherein said digital data processing means includes at least standardizing value register means for storing standardizing values derived by placement of an appearance standard of the specimens whose appearance is to be measured in the specimen holder means and deriving standardizing values from the standard specimen output signals obtained from the ouput of the analog to digital converter means while measuring the standard, specimen register means for storing input specimen signal values obtained from the output of the analog to digital encoder means and representative of the appearance values of a test specimen being measured, and central processing unit means for multiplying the specimen signal values by the standardizing values to thereby derive a standardized specimen signal output for display or other use which is representative of the appearance characteristics of a test specimen standardized relative to the standard.

19. A scanning spectrophotometer-digital data processing system for appearance measurement according to claim 1 wherein the standardizing value register means comprises a plurality of operator keyboard accessed standard assigned values register means for storing known standard values of transmittance, reflectance with specular reflectance components included and reflectance with specular reflectance components excluded for the appearance standard placed in the specimen holder means during derivation of the standardizing values, said central processing unit means serving to divide the standardizing specimen digital electric output signals obtained from the output of the digital to analog converter means with the appearance standard placed in the specimen holder means by the standard assigned values stored in the standard assigned value register means and deriving the quotient, calibration factor multiplier register means comprising a part of the standardizing register means for storing the quotients for use as calibration factor multipliers in the standardizing process, said calibration factor multipliers being the values used by the central processing unit means while standardizing specimen signal values obtained from the output of the analog to digital converter means while measuring a test specimen for its appearance characteristics.

20. A scanning spectrophotometer-digital data processing system for appearance measurements according to claim 19 wherein said digital data processing means further includes zero adjust value register means for storing zero adjust values determined by placing an opaque member in the light measurement path in advance of the monochromator means, means for deriving zero adjust signal values for each of the plurality of separate different wavelength monochromatic light beams from the output of the analog to digital converter means with the opaque member still in place, and means for storing the values in the zero adjust register means, said central processing unit means serving to subtract said zero adjust values from the input specimen signal values prior to standardization.

21. A scanning spectrophotometer-digital data processing system for appearance measurements according to claim 20 wherein said system is designed to measure at least the characteristics of transmittance, reflectance with specular reflectance components included and reflectance with specular components excluded for each test specimen being processed and further including sphere efficiency factor calculation program register means for both reflectance measurements and wherein, said central processing unit means further serves to process reflectance measurement signals derived according to claim 20 by a respective reflectance specular included or reflectance specular excluded sphere efficiency factor calculation program derived from said sphere efficiency factor calculation program register means to thereby derive true reflectance measurements corrected for effect of the specimens on the intensity of the light from the integrating light sphere as a diffuse light source.

22. A scanning spectrophotometer-digital data processing system for appearance measurements according to claim 21 wherein said system further includes C.I.E. $\bar{x}, \bar{y}, \bar{z}$ observer function read only memory register means for storing the C.I.E. $\bar{x}, \bar{y}, \bar{z}$ functions, and a programmed register for each illuminant used with the system, respective illuminant tables of spectral power distribution values register means the contents being keyboard accessible to an operator of the system for supply to the central processing unit means along with the C.I.E. $\bar{x}, \bar{y}, \bar{z}$ functions, and the standardized and zero adjusted test specimen signal values representative of the appearance characteristics of a test specimen being measured, said central processing unit further serving to multiply the C.I.E. functions times a selected illuminant, times the standardized and zero adjusted test specimen signal values of reflectance or transmittance as the case may be and summing the results obtained over the visible spectrum to thereby derive the tristimulus C.I.E. - X, Y, Z (1931) Standard Colorimetric System values of a test specimen for display or other use.

23. A scanning spectrophotometer-digital data processing system for appearance measurements according to claim 22 further including operator keyboard accessed uniform color scale program read only memory register means for permanently storing uniform color scale computation programs for deriving color scale values L, $a, b$; Y, $x, y$ and the like automatically from the C.I.E. X, Y, Z tristimulus values derived by the central processing unit means according to claim 22, said central processing unit means further serving to derive the color scale values L, a, $b$; Y, $x, y$ and the like of a test specimen for display or other use automatically under the control of a selected uniform color scale program called out by an operator of the system from the uniform color scale read only register means.

24. A scanning spectrophotometer-digital data processing system for appearance measurements according to claim 23 further including reference color scale register means for performing color difference measurements, said central processing unit means upon command serving to store color scale reference values in said reference color scale register means obtained from a color reference placed in the specimen holder means with respect to which differences of test specimens in color scale are to be measured, operator controlled keyboard operated means for alternatively storing keyboard entered color scale reference values in said reference color scale register means, said central processing unit means further serving to subtract the color scale reference values in the reference color scale register means from the test specimen color scale values derived according to claim 23 to thereby derive color difference values between the test and reference specimens for display or other use.

25. A method for making appearance measurements with a scanning spectrophotometer-digital data processing system having a stabilized specimen illumination means, specimen holder means, monochrometer means, electro-optic detector means responsive to light directed thereon from said monochrometer means, analog to digital converter means responsive to the output from said electro-optic detector means, digital encoder means operatively synchronized in operation with said monochrometer means and digital data processing means; said method of appearance measurement comprising illuminating a test specimen to be examined and supported in said specimen holder means with stabilized light from said stabilized source of illumination, producing an output single beam of light modulated with appearance characteristics information pertaining to a specimen being examined, directing the output single beam of light onto the monochrometer means and deriving a plurality of separated, different wavelength monochromatic single light beams representative of the appearance characteristics of a specimen being examined, serially directing the separate different frequency monochromatic single light beams onto the electrooptic detector means for converting the same to a plurality of separate different electric signals representative of the visual response characteristics of a specimen being examined at each wavelength, electrically converting the different electric signals thus derived for each wavelength the output from the encoder means operated synchronously with the monochrometer means and processing the characteristic digital electric output signals to derive output electric signals for display or other use which are indicative of the appearance characteristic of a specimen being examined.

26. The method of appearance measurement according to claim 25 further including storing standardizing values derived by placement of an appearance standard of the test specimens whose appearance is to be measured in the specimen holder means and deriving standardizing values from the standardizing specimen digital electric output signals obtained from the output of the analog digital converter means of the instrument while measuring the standard, storing the input specimen signal values obtained from the output of the analog to digital converter mean and representative of the appearance values of a test specimen being measured, and multiplying the test specimen signal values by the standardizing values to thereby derive a standardized specimen signal output for display or other use which is representative of the appearance characteristics of a test specimen standardized relative to the standard.

27. The method of appearance measurement according to claim 26 further including storing zero adjust values determined by placing an opaque member in the light measurement path in advance of the monochrometer means and deriving the zero adjust signal values for each of the plurality of separate different wavelength monochromatic light beam from the output of the analog to digital converter means for storage and subsequent use, and subtracting the zero adjust values from the input specimen signal values prior to standardization.

28. The method of appearance measurement according to claim 27 further comprising storing known standard values of transmittance, standard values of reflectance with specular reflectance components included and standard values of reflectance with specular reflectance components excluded for the appearance standard placed in the specimen holder means during derivation of the standardizing values, dividing the standardizing specimen digital electric output signals obtained from the output of the digital to analog converter means with the appearance standard placed in the specimen holder means by the standard assigned values, storing the quotients thus obtained for use as calibration factor multipliers in the standardizing process, and thereafter multiplying test specimen signal values obtained from the output of the analog to digital converter means while measuring a test specimen for its appearance characteristics with the calibration factor multipliers to thereby standardized the test specimen signal values relative to the standard.

29. The method of appearance measurement according to claim 28 further including calculating in said digital data processing means, illuminating light efficiency factors for both reflectance type measurements with specular reflectance components included and with specular components excluded, and further multiplying the zero adjusted and standardized reflectance measurements signals derived in accordance with claim 28 by an efficiency factor derived from the illuminating light efficiency factor calculations to thereby derive a true reflectance measurement corrected for illuminating light source inefficiencies.

30. The method of appearance measurement according to claim 29 further including storing in a read only memory register means comprising a part of the digital data processing means the C.I.E. $\bar{x},\bar{y},\bar{z}$ functions and tables of spectral power distribution for each illuminant, multiplying the C.I.E. $\bar{x}, \bar{y}, \bar{z}$ function times a selected illuminant, times the standardized and zero adjusted test specimen signal values of reflectance or transmittance derived according to claim 29 and summing the results obtained in 10 nanometer wavelength intervals over the visible spectrum to thereby derive the tristimulus C.I.E. X, Y, Z (1931) standard colorimetric system value of a test specimen for display or other use.

31. The method of appearance measurement according to claim 30 further including storing in an operator keyboard accessed preprogrammed register selected uniform color scale computation programs for automatically controlling the central processing unit of the digital data processing means to derive color scale values L, a, b; Y, x, y and the like automatically from the C.I.E. X, Y, Z tristimulus values derived according to claim 30 for display or other use.

32. The method of appearance measurement according to claim 31 further including storing in a reference color scale register comprising a part of the digital data processing means color scale reference values obtained either from a color reference placed in the specimen holder means with respect to which differences of test specimens in color scale are to be measured or alternatively storing known color scale reference values entered by an operator through the keyboard and thereafter subtracting the color scale reference values stored in the reference color scale register from test specimen color scale values derived according to claim 31 to thereby derive color difference values between the test and reference specimens for display or other use.

33. The method of appearance measurement according to claim 25 further including storing zero adjust values determined by placing an opaque member in the light measurement path in advance of the monochrometer means or a light trap at the reflectance port and deriving the zero adjust signal values for each of the plurality of separate different wavelength monochromatic light beams from the output of the analog to digital converter means for storage and subsequent use, and subtracting the zero adjust values from the input specimen signal values prior to standardization.

* * * * *